United States Patent [19]

Abraham-Fuchs et al.

[11] Patent Number: 5,417,211

[45] Date of Patent: May 23, 1995

[54] METHOD FOR THE CLASSIFICATION OF FIELD PATTERNS GENERATED BY ELECTROPHYSIOLOGICAL ACTIVITIES

[75] Inventors: Klaus Abraham-Fuchs, Erlangen; Martin Schlang, Munich; Johann Uebler, Nuernberg, all of Germany

[73] Assignee: Siemens Aktiengesellschaft, Munich, Germany

[21] Appl. No.: 101,043

[22] Filed: Aug. 3, 1993

[30] Foreign Application Priority Data

Aug. 5, 1992 [DE] Germany ............... 42 25 894.4

[51] Int. Cl.⁶ .............................................. A61B 5/05
[52] U.S. Cl. ............................ 128/653.1; 395/23; 395/924
[58] Field of Search ............ 128/653.1; 324/244, 324/248, 260; 395/20, 21, 23–25, 924; 364/413.02, 413.26

[56] References Cited

U.S. PATENT DOCUMENTS

| | | |
|---|---|---|
| 4,974,602 | 12/1990 | Abraham-Fuchs et al. |
| 5,092,353 | 3/1992 | Spitzer et al. |
| 5,152,288 | 10/1992 | Hoenig et al. |
| 5,218,529 | 6/1993 | Meyer et al. ............... 395/924 X |
| 5,255,362 | 10/1993 | Brandstetter ............... 395/25 X |
| 5,280,792 | 1/1994 | Leong et al. ............... 128/702 |

FOREIGN PATENT DOCUMENTS

0477434  4/1992  European Pat. Off.

OTHER PUBLICATIONS

"Sleep Classification in Infants Based on Artificial Neural Networks"; Pfurtscheller, et al., Biomed Technik, vol. 37 No. 6 (1992), pp. 122–130.

"Improving Learning Behavior and Discrimination of Neural Networks Used for Pattern Recognition in Biosignals", Hermann, et al., Biomed Technik, vol. 37, No. 4 (1992), pp. 69–72.

"Personal Computer System for ECG, ST-Segment Recognition Based on Neural Networks", Suzuki, et al., Med. & Biol. Eng. & Comput., vol. 30 (Jan. 1992), pp. 2–8.

*Primary Examiner*—Ruth S. Smith
*Attorney, Agent, or Firm*—Hill, Steadman & Simpson

[57] ABSTRACT

A method for classifying field patterns generated by electrophysiological activities occurring inside the body of a living subject includes the steps of measuring field patterns arising as a result of the electrophysiological activities outside the body of the subject using a multi-channel measuring apparatus, generating feature vectors corresponding to the measured field patterns, supplying the feature vectors to an adaptive classifier, and training the adaptive classifier with training field patterns which have been generated by a localizable surrogate model of the electrophysiological activity. The method includes the further step of generating a probability value for each field pattern at an output of the adaptive classifier which indicates the probability with which each field pattern can be generated by a selected localizable surrogate model. This classification method greatly reduces the number of possible patterns which must be reviewed by a physician in order to evaluate the electrophysiological activity of the subject.

14 Claims, 3 Drawing Sheets

METHOD FOR THE CLASSIFICATION OF FIELD PATTERNS GENERATED BY ELECTROPHYSIOLOGICAL ACTIVITIES

BACKGROUND OF THE INVENTION

1. Field of the Invention

The present invention is directed to a method for the classification of field patterns that are generated by electrophysiological activities occurring inside the body of a living subject and which are measured outside the subject with a measuring apparatus, having an adaptive "teachable" classifier that is connected to the measuring apparatus.

2. Description of the Prior Art

U.S. Pat. No. 5,092,343 discloses a method of the type generally described above. An electromyographic signal, for example, taken from a muscle via a needle, is sampled and searched for typical signal shapes. The typical signal shapes that are recognized are then supplied to means for classification that allocate the typical signal shapes to pathological conditions. The means for classification comprise a neural network that is trained with data of normal groups and patient groups.

An article by Pfurtscheller et al., "Sleep Classification in Infants Based on Artificial Neural Networks", in Biomedizinische Technik, Vol. 37, No. 6/1992, pages 122–130 discloses the formation of data vectors, that are evaluated with the assistance of two neural networks, for sleep classification from polygraphic data, i.e. data of a plurality of events and phenomena such as EEG, EOG, EMG, ECG, etc. The neural networks were previously trained with classifications entered by a person who is knowledgeable in this field.

A measuring apparatus with which spatial field patterns of the type described above can be measured is disclosed in European Application 0 359 864. The measuring apparatus is a multi-channel measuring apparatus and is also referred to as biomagnetic measuring system. The field patterns of extremely weak magnetic fields that are generated by electrophysical activities occurring inside the body of a living subject can thus be measured. The multi-channel measuring apparatus includes a multi-channel gradiometer arrangement that is coupled to a multi-channel SQUID arrangement. The signals are measured at spatially separate locations at identical times with the multi-channel measuring apparatus, and combine to form the field patterns, which are utilized to construct a surrogate model of the electrophysiological activity. A sphere and an infinite half-space of uniform conductivity wherein a source of magnetic signals is located are used therein as the surrogate model for activities.

Both magnetoencephalograms (MEG) and magneto cardiograms (MCG) can be measured with the biomagnetic measuring system. The principal goal for the evaluation of the MEG or MCG recordings is a three-dimensional, non-invasive localization of sources of pathological electrophysiological activities. To that end, that pathological activities or events must be identified from the MEG or MCG registrations in a first step. Pathological events that occur in the cerebrum are, for example, spike activity, steep waves, slow waves, K-complexes or rhythmic activity in the theta or delta region.

The registration duration is on the order of magnitude of 5 through 10 minutes, which corresponds to approximately 30 through 60 pages of registration. A skilled physician requires approximately 10 seconds for identifying the pathological events for one page, which is in the form of a 30 cm long paper recording or as an image on a computer picture screen. This means that approximately 30 through 60 "pages" must be searched for pathological events. This work is generally extremely time-intensive and exhausting. Important data sections can also be very easily overlooked.

However, all selected pathological activities or events cannot be located with the same reliability or precision. Thus, for example, the electrophysiological activity must be capable of being represented by a model. The selection of the events that are utilized for source localization also substantially influences the reliability of the localization, whereby the signal-to-noise ratio is critical. When similar events that follow one another are averaged, the success of the event recognition is dependent on a selected comparison result with which the events to be averaged are identified.

SUMMARY OF THE INVENTION

It is an object of the present invention to provide a method with which field patterns that can be localized with the assistance of a model can be identified from the measured field patterns, even if noise is superimposed on the measured field patterns.

This object is achieved in a method in accordance with the present invention by obtaining measured signals using a multi-channel measuring apparatus and classifying the resulting field patterns using an adaptive or "teachable" classifier having a plurality of input channels to which feature vectors that are representative of the measured field patterns are supplied. The adaptive classifier is trained with training field patterns that have been generated by a localizable surrogate model of the electrophysiological activity, and a probability value that indicates the probability with which every field pattern can be generated by the localizable model is generated for each field pattern at an output channel. By contrast to many known methods such as, for example, the methods set forth earlier that automatically search the measured values measured by the measuring apparatus for pathological events, the present invention leaves the definition of the pathology of the events up to the physician. Inventively, the method recognizes those field patterns that can be localized by a prescribed model source or by a surrogate model despite a more or less pronounced superimposition with noise. The method classifies the field patterns into two groups:

(1) field patterns that can be generated by the prescribed surrogate model with high probability and which, consequently, can be localized; and (2) field patterns that cannot be described by the surrogate model because the surrogate model does not adequately or precisely enough describe the underlying physiological process.

Due to the many possible, slightly varied forms of the field patterns, the division into localizable and non-localizable events can be especially reliably resolved by a neural network.

In an embodiment of the invention, the feature vectors are generated in a pre-processing unit from the measured field patterns. The pre-processing unit is arranged between the multi-channel measuring apparatus and the adaptive classifier.

It is advantageous for the classification to norm the measured values of the field patterns. Information that is unimportant for the classification is thus removed from the field patterns.

In another aspect of the invention the pre-processing unit includes an amplitude norming means for norming the amplitudes of the measured values of the field patterns transmitted in every channel. The classification of the field patterns is thus only dependent on the mutual relationship between the measured values in the individual measured value channels.

In another aspect of the invention the adaptive classifier is trained with a second class of training field patterns that are generated by at least one non-localizable surrogate model. The training of the adaptive classifier can ensue via a computer simulation.

In a further aspect of the invention, the training field patterns have noise superimposed on them. Due to the superimposition of noise, the neural network is trained with frequently varied training field patterns that correspond to the field patterns measured in practice. A localization becomes too imprecise when the signal-to-noise ratio in the field patterns falls below a value. This is taken into consideration in the training of the neural network.

In another aspect of the invention, the plurality of channels in the multi-channel measuring apparatus is at least 30 and the neural network has hidden neurons whose number is approximately equal to one and one-half times the plurality of channels of the multi-channel measuring apparatus. The plurality of hidden neurons in the neural network is a compromise between the plurality of required training field patterns and the comprehensive capability of the neural network of recognizing localizable field patterns. The plurality of input neurons likewise defines the plurality of hidden neurons. As a result of this selected arrangement, an optimum is achieved with respect to the classification speed and precision of the classification of the measured and registered field patterns.

In another aspect of the invention, the multi-channel measuring system and the output channel of the adaptive classifier is connected to an image display unit that, in addition to indicating the chronological curve of the field patterns, indicates the probability value with which the respective field pattern can be generated by the surrogate model. The diagnosing physician need thus concentrate during the evaluation of the multi-channel registrations only on the field patterns that can be localized at all by the source model employed. Other field patterns which are in fact significant for pathological activities, but which cannot be localized, need not be investigated in the registrations.

In another aspect of the invention, a threshold means is connected to the output channel, which reproduces the probability value when it lies above a threshold and reproduces the value zero when the probability value lies below the threshold. When the probability is low, then this simultaneously means that a localization of the activity is affected by an excessively large error, so that a diagnosis becomes unreliable.

In a further aspect of the invention, the threshold means includes a timer means that sets the probability value to zero when it does not lie above the threshold for at least a minimum chronological duration. This proceeds from the perception of the inventors that electrophysical activities have a minimum duration that is prescribed by the aggregate action potential. A sporadic, brief-duration rise of the probability is not possible for electrophysiological reasons in a pathological activity. A briefly elevated probability is therefore suppressed and is not displayed together with the field patterns.

In another embodiment, a weighting unit is connected to the multi-channel measuring system. The weighting unit forms a weighting factor dependent on the plurality of positive and negative field values in the field pattern, and a multiplication unit is connected to the weighting unit and to the output channel. The multiplication unit multiplies the probability value supplied by the output neuron by the weighting factor and generates a modified probability value. The localization of electrophysiological activities can ensue most precisely when an ideal dipolar field pattern is present. Given a dipolar field pattern, the multi-channel measuring apparatus measures a positive amplitude and a negative amplitude with an identical plurality of measuring channels. The localization precision is degenerated with an increase in the plurality of measured values having an identical operational sign, down to the poorest case of a completely monopolar field. Only one polarity is measured by the multi-channel measuring apparatus given a monopolar field pattern. This dependency of the localization precision is not introduced into the training phase of the adaptive classifier, but is implicitly learned. The evaluation of the polarity in the field pattern can be more simply undertaken by the weighting unit than by a correspondingly trained classifier.

In another aspect of the invention, the field patterns are biomagnetic field patterns. By contrast to electrical field patterns that are likewise generated by an electrophysiological activity, the magnetic field patterns can be evaluated via simple surrogate models for localization of the activity. When the localization is to ensue on the basis of measuring the electrical field patterns, the surrogate model must take the different conductivity in the inside of the subject into consideration.

In another aspect of the invention, the surrogate model is composed of an electrical dipole that is arranged in a space which has a uniform electrical conductivity. Many pathological activities can be diagnosed with this simple model.

DESCRIPTION OF THE PREFERRED EMBODIMENTS

Figure 1:
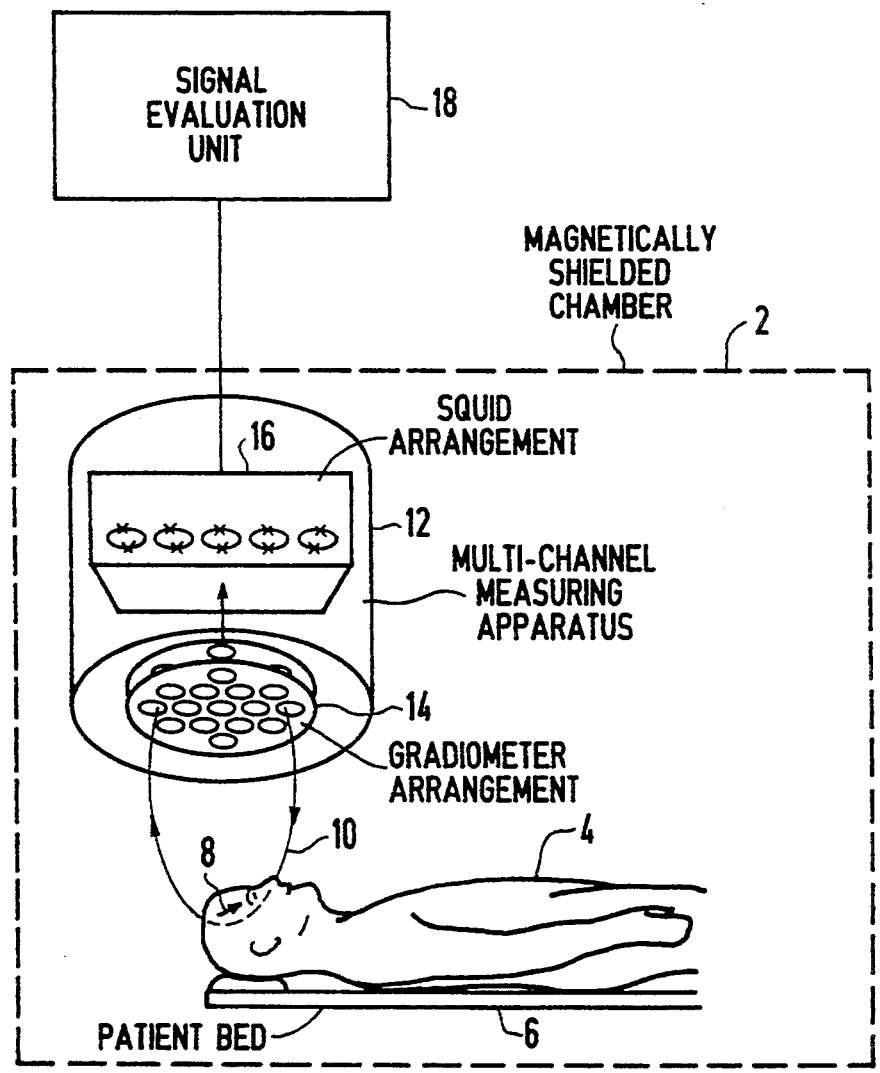
FIG. 1 shows the structure of a biomagnetic measuring system with which the field patterns to be classified in accordance with the inventive method are measured.

The method for classifying field patterns is described herein in the context of a biomagnetic measuring system with which electrophysiological activities are localized via a magnetic field measurement. Disturbances can thereby be generated outside as well as inside the patient. FIG. 1 schematically shows a magnetic shielded chamber 2 within which externally generated disturbing fields are, shielded for the most part. A patient 4 to be examined is situated on a patient bed 6 arranged in the shielded chamber 2. Electrophysiological activities, symbolized by an arrow 8, generate an electrical field pattern and a magnetic field pattern; only the magnetic field pattern 10 is evaluated here. To that end, the magnetic field is measured with a multi-channel measuring apparatus 12 above the patient 4. The multi-channel measuring apparatus 12 includes a multi-channel gradiometer arrangement 14 having gradiometers that are arranged spatially separated, and which only acquire the gradients of the magnetic field distribution, and thus already suppress uniform noise fields in the measurement. For clarity, a multi-channel gradiometer arrangement 14 having 15 individual gradiometers is shown; in practice, multi-channel gradiometer arrangements 14 having more than 30 channels, for example 37 channels, are employed. The gradiometers in the multi-channel gradiometer arrangement 14 are respectively connected to a SQUID (superconducting quantum interference device). The multi-channel SQUID arrangement 16 and the multi-channel gradiometer arrangement 14 are arranged in a cryostat and are kept at so low a temperature therein that a superconducting state prevails.

The multi-channel measuring arrangement 12 can be rigidly held in an examination position with a stand. The examination position prescribes the measurement locations of the gradiometers. In the illustrated examination position, the field patterns of cerebral activities are measured. The measured signals, measured in chronological succession at the measurement locations, are forwarded to a signal evaluation unit 18 that both indicates the chronological behavior of the measured signals and identifies an equivalent current dipole whose theoretical field pattern comes closest to the measured field pattern for the selected field patterns. A complete surrogate model is composed of the location of the equivalent current dipole, the dipole strength, and the dipole direction. The space wherein the current dipole is arranged also is part of the surrogate model. The space wherein the equivalent current dipole is located in the surrogate model for cerebral activities is a sphere having uniform conductivity and is an infinite half-space having uniform conductivity for cardiological activities.

Figure 2:
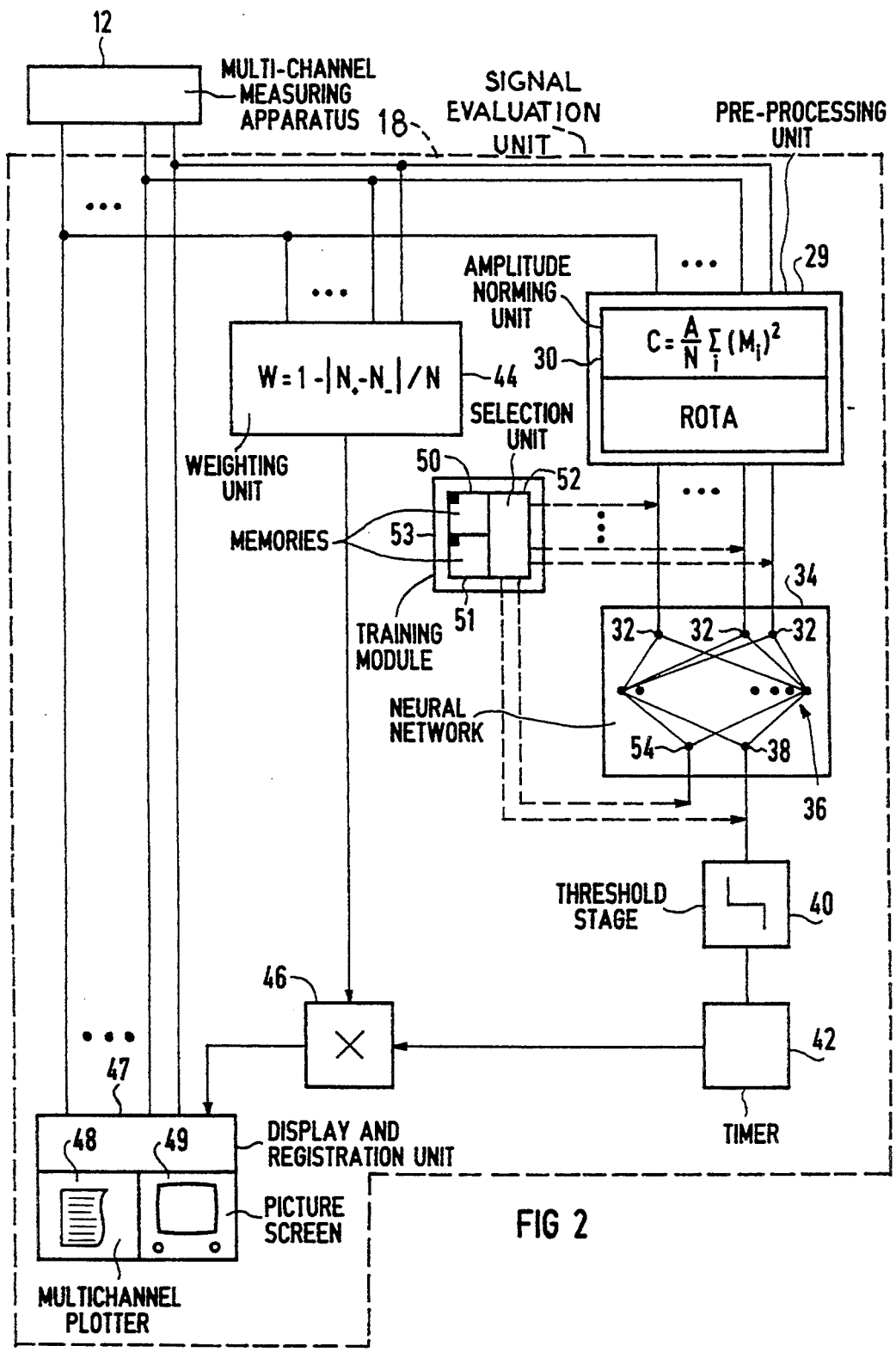
FIG. 2 is a block diagram of a method for the classification of field patterns in accordance with the principles of the present invention.

FIG. 2 shows the method for classification of field patterns in a block diagram. Each measurement channel of the multi-channel measuring apparatus 12 is uniquely connected to an input channel 32 of an adaptive classifier network 34 via a pre-processing unit 29, which includes an amplitude norming unit 30. The plurality of input channels 32 thus corresponds to the plurality of measurement channels in the multi-channel measuring arrangement 12. This plurality is 37 in this case. The amplitude norming unit 30 in the pre-processing unit 29 norms the measured values of the field patterns in order to enhance the classification precision. Thus, for example, the measured field patterns are invariant with respect to a rotation around the symmetry axis of the multi-channel gradiometer arrangement 14. The field pattern can therefore be turned into a standard position before the classification, as illustrated in FIG. 2 by the module ROTA. The information about the rotational angle—which is superfluous here—is thus removed from the field patterns. As warranted, the measured values of the field patterns must be interpolated dependent on the rotational angle and on the geometry of the multi-channel gradiometer arrangement 14. Without an interpolation, the rotation means nothing more than a cyclical interchange of the connections between the multi-channel gradiometer arrangement 14 and the input channels 32 of the classifier 34. The sequence of the interchange, however, is undertaken dependent on the measured field pattern.

The amplitude norming unit 30 norms the amplitudes of the measured values, so that the aggregate effective value over the amplitudes of all measured values of a field pattern is the same for all field patterns. A factor A for the measured values of the field pattern is thereby identified for every field pattern according to the following equation:

$$\frac{A}{N} \sum_{i=1}^{N} (M_i)^2 = C$$

wherein N is the plurality of measuring channels, $M_i$ is the measured value in the $i^{th}$ measuring channel, C is a constant that is valid for all field patterns, and A is the sought factor.

A two-layer, completely connected, forward-coupled neural network having sigmoidal non-linearities in the neurons is utilized as the adaptive classifier 34, whereby the input neurons and output neurons of the network represent the input channels and output channels of the adaptive classifier 34.

Such a neural network is described by J. Hertz et al. in "Introduction to the Theory of Neural Computation", Adison Wesley, Redwood City, 1991. The neural network 34 has 50 hidden neurons 36; the plurality of hidden neurons 36 is approximately equal to one and one-half times the plurality of channels of the multi-channel measuring apparatus 12. This yields an optimum in the classification rate. An output neuron 38 supplies a probability value that indicates the probability with which the field pattern present at the input side can be generated with a surrogate model of an equivalent current dipole in a uniform, conductive sphere. The direction as well as the location of the equivalent current dipole is thus determined in the signal evaluation unit 18.

The output neuron 38 is connected to a threshold stage 40 that only forwards probability values that lie above a threshold. A threshold of 0.3 is meaningful. Since, however, a sporadic, brief-duration rise of the probability value is not possible for physiological reasons, a timer 42 follows the threshold stage 40, which sets the probability value to zero when it does not lie above the threshold for a minimum duration of 6 ms in this case.

A weighting unit 44 is likewise connected to the measuring channels of the multi-channel measuring apparatus 12 parallel to the neural network. The weighting unit 44 utilizes the empirical knowledge about the position of the localization of equivalent current dipoles and generates a weighting value that lies between zero and one in addition to the probability value of the neural network. An equivalent current dipole can be most precisely localized when the field pattern ideal is dipolar. An ideally dipolar field pattern has an identical plurality of measured values with a positive amplitude and with a negative amplitude. The localization precision decreases with decreasing dipolarity of the field pattern and is poorest given a completely monopolar field, i.e. all measured values have the same amplitude polarity. The weighting unit 44 generates a weighting value W according to the equation $$W = 1 - |(N_+ - N_-)/N|,$$

wherein N is the total number of measured value channels, $N_+$ is the plurality of measured values having a positive field amplitude and $N_-$ is the plurality of measured values having a negative field amplitude.

The output of the weighting unit 44 is connected to a first input of a multiplication unit 46, and the output of the timer 42 is connected to a second input of the multiplication unit 46. The probability value supplied by the neural network 34 is thus multiplied by the weighting value output by the weighting unit 44. The multiplication unit 46 generates a modified probability value of an output.

The output of the multiplication unit is connected to a display and registration unit 47 which is also connected to the outputs of multi-channel measuring arrangement. The display and registration unit 47 has a multi-channel plotter 48 and a picture screen 49 with which the individual measured values and the modified probability value can be registered and/or displayed.

The neural network 34 must first be trained as to how the field patterns 10 are to be classified. Its performance capability in the classification is critically dependent on the training data employed. As a consequence of the many possible field patterns that can be generated by a surrogate model and that may also be potentially superimposed with noise, a large quantity of training data that can be generated in a computer simulation is required for the training of the neural network 34. A first class of training field patterns, which is referred to as "correct class", contains field patterns that are generated by a localizable surrogate model. A second class of training field patterns, which is referred to as "wrong class", contains non-localizable field patterns.

For generating the training data for the "correct class", one proceeds on the basis of an equivalent current dipole that is arranged in a sphere having a uniform conductivity. Current dipoles that are located in the entire half of the sphere that faces toward the multi-channel measuring apparatus 12 and current dipoles that are arranged a short distance beneath this half-sphere can be localized. The sphere radius typically amounts to 9 cm. A smaller, central sphere having a radius of 2 cm is excluded because current dipoles that lie within this small sphere only generate extremely small magnetic fields outside the model sphere. This essentially hemispherically shaped region is referred to below as "region of interest" or ROI.

A simulated multi-channel measuring arrangement that corresponds to the multi-channel measuring apparatus 12 is arranged 12 cm above the ROI. The training field patterns for the "correct class" are generated by statistically distributed current dipoles within this ROI. The localization parameters as well as the orientation parameters of the equivalent current dipole are thereby statistically varied. The field patterns are normed to an effective value of 1 pT.

The field patterns are thus independent of the amplitude and the amplitude does not enter into the classification by the neural network 34. In general, the training field patterns are pre-processed in the same way as is carried out for the measured field patterns by the pre-processing unit 29. This class of training data is referred to below as Class I.

What types of field patterns can occur and be measured at all must be taken into consideration for generating the training field patterns for the "wrong class". In addition to field patterns that arise from a focal activity and that can be generated by the surrogate model, a great part of the field patterns are generated by multi-focal activities that are distributed over the entire examination region. It is assumed here that the plurality of current dipoles that participate in the multi-focal activities is limited, so that the field patterns nonetheless exhibit a systematic structure. For generating the corresponding training field patterns, three current dipoles are simultaneously varied here, these being statistically distributed in the ROI. In the following, the field patterns of the statistically distributed, three current dipoles are classified into a Class II. All other complex activities, including the periods of extremely low activities, where noise dominates, are simulated by random noise patterns over all measuring channels; the noise yields Class III. The amplitudes of the field patterns of Classes II and III are also normed to an effective value of 1 pT.

The computer simulation first produces a statistical mix of the field patterns of all three classes and stores the field patterns and the class belonging thereto. In those cases wherein the field patterns are generated by one or three equivalent current dipoles, the parameters of the equivalent current dipoles are likewise stored.

The measured values of the field patterns that can be simulated by equivalent current dipoles occur with extremely different signal-to-noise ratios in practice. Since the capability of the neural network 34 for classification is also dependent on the noise level, the training field patterns must contain different noise levels. To that end, noise-free patterns as well as patterns having a relatively low signal-to-noise ratio of 3 are produced. The signal-to-noise ratio for the noise-infested training field patterns is defined as the ratio of the effective value of the noise-free field patterns divided by the effective value of the noise that is added.

A reclassification of the field patterns is required before these field patterns can be utilized for training the neural network 34. The exact objective for the classification of field patterns is: field patterns should be recognized that have a high probability of arising from a focal activity that can be described and localized by an equivalent current dipole. Not all field patterns of Class I meet this criterion because some of the statistically distributed, equivalent current dipoles can lie in the proximity of the center and thus do not produce any noteworthy magnetic field. In the multi-focal Class II, on the other hand, one of the three equivalent current dipoles can dominate over the other two because it is arranged significantly closer to the multi-channel measuring apparatus 12 than are the other two. Two of the three current dipoles can also mutually cancel. The neural network 34 would thus be misled to learn such patterns as multi-focal field patterns. For this reason, it is necessary to previously subject the training field patterns of Class I and Class II to a current dipole localizing method and to compare the result of the localization to the true or stored parameters of the equivalent current dipole. An arbitrarily selected limit of, for example, 1.5 cm localizing precision, i.e. the difference between the localization result and the true dipole location, is therefore interposed. All patterns of Classes I and II that can be successfully localized within the above-recited limit are consequently classified into the first "correct class". All field patterns of the original Class I that cannot be successfully localized are classified into the second "wrong class". All non-localized field patterns of Class II, like the field patterns of Class III, are entered in the second class. These training field patterns of the first and second class generated in this way are used in order to train the neural network 34. In FIG. 2, the training field patterns of the first class are deposited in a first memory 50 and the training field patterns of the second class are deposited in a second memory 51.

The training data are used in order to determine the internal connections, the so-called weightings of the network 34. At the beginning of the training, all weightings are occupied with random values. For training the network 34, a field pattern from the first or second class is called in from the memory 50 or 51 by a selection unit 52 having a random generator and is supplied to the input neurons 32. In FIG. 2, the training phase is illustrated by the broken-line connections to a training module 53 that comprises the memories 50, 51 and the selection unit 52.

In addition to using the output neuron 38, another output neuron 54 is required for training the neural network 34. The output neuron 38 supplies a probability value for the probability that the field pattern can be generated by an equivalent current dipole. By contrast, the output neuron 54 supplies a probability value identifying the probability that the field pattern cannot be generated by an equivalent current dipole. The sum of the two probabilities is not necessarily "1" because a non-linear network 34 is involved. In the classification of the field patterns, that output neuron 38 or 54 whose value is highest has "won". When, for example, a field pattern generates the value "0.6" at the output neuron 38 and the value "0.55" at the output neuron 54, the field pattern has been recognized as being localizable.

This division is compared to the true classification of the field pattern. With the assistance of the error tracking corresponding to that recited by D. E. Rummelhart et al. in the article "Parallel distributed processing", MIT Press, 1986, the weightings in the network 34 are adapted such that the difference between the output value is minimized on average over all training field patterns. The training process is repeated until the correct classification rate of the network 34 is maximum. It has proven to be adequate that an optimum classification rate with 10,000 training field patterns was achieved after $1.5 \times 10^7$ training runs of the individual patterns. The training itself requires several hours of computer time on a RISK work station, however, it need only be implemented once. By contrast, the classification process of the measured field patterns is extremely fast, and lies on the order of magnitude of a few minutes for field patterns measured in a time span of 1 minute that were registered with a scanning rate of 400 Hz.

Although the training was only carried out for a single, simulated position of the multi-channel measuring arrangement 12 with reference to the ROI, one can expect similar conditions in most magnetoencephalograms due to the spherical symmetry. Deviations can arise due to an enlarged spacing of the multi-channel measuring apparatus 12 or due to a lateral shift of the multi-channel measuring apparatus 12 with reference to the center of the ROI. When, however, the size of the human head and the size of the area of the multi-channel measuring apparatus 12 are taken into consideration, then these deviations do not amount to more than a few centimeters. Such small deviations have no significant influence on the training field patterns.

When the arrangement of the gradiometers in the multi-channel gradiometer arrangement 14 is modified, the neural network 34 must also be fundamentally re-trained. Small modifications in the arrangement, however, can be compensated by interpolation of the field patterns.

In general, the method for the classification of field patterns can also classify electrical field patterns from electroencephalograms or electrocardiograms. However, the surrogate model must now take the different conductivity of the body into consideration because field distortions that deteriorate the localization precision occur due to conductivity changes in the ROI.

Figure 3:
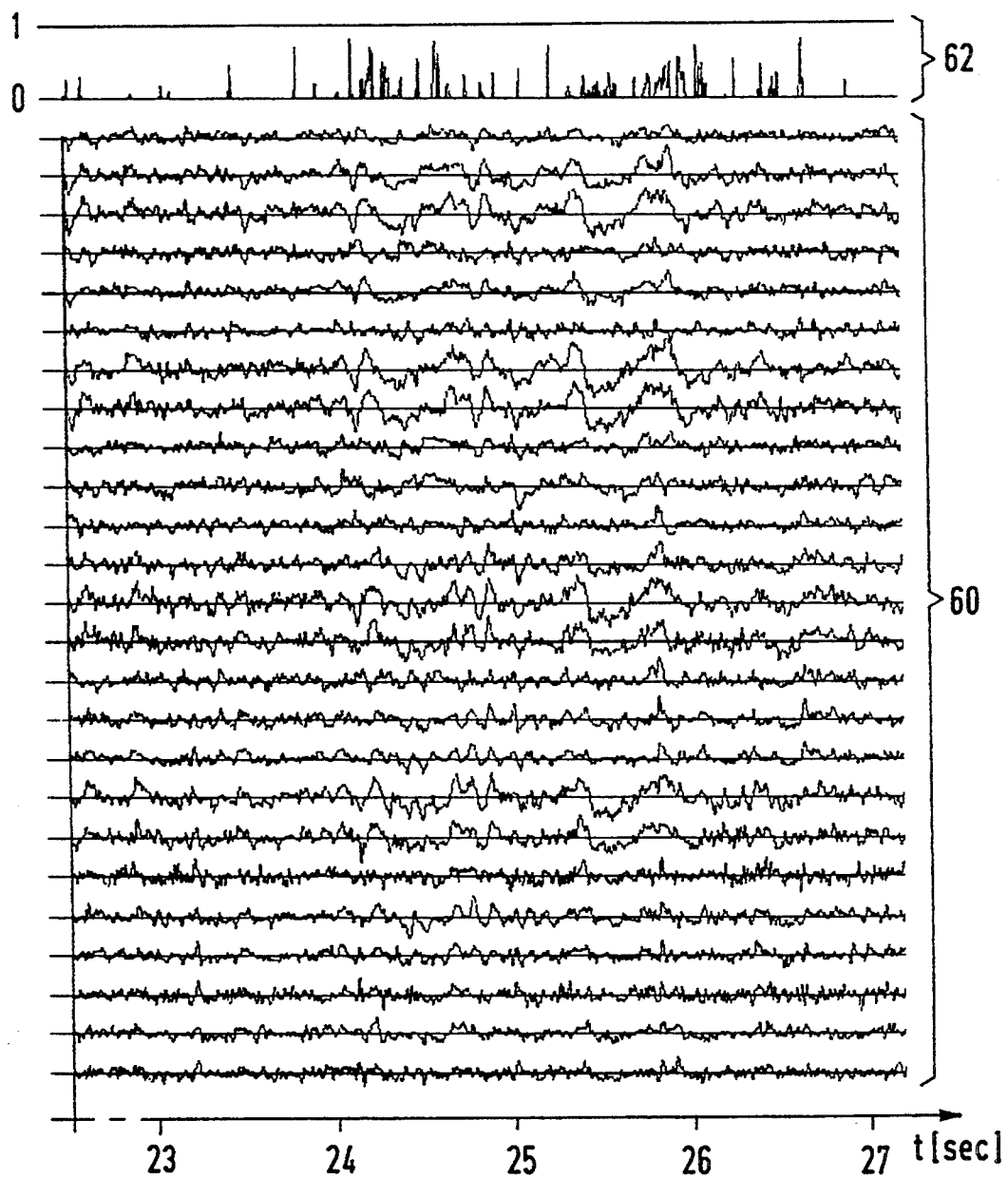
FIG. 3 shows a registration of field patterns that are present as measured values measured by a multi-channel measuring apparatus, as well as the display of the probability belonging to the field patterns in accordance with the inventive method.

FIG. 3 shows a registration of field patterns measured with a multi-channel measuring apparatus 12. A field pattern is established by the measured values 60 measured at the same time. The probability value that belongs to every field pattern and indicates the probability with which the field pattern can be generated by the selected surrogate model is entered above the measured values 60 in a diagram 62. The probability value lies between 0 and 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for classifying spatial field patterns generated by electrophysiological activities occurring in the body of a living subject, comprising the steps of:
   generating a plurality of training field patterns respectively from a plurality of localizable surrogate models and at least one non-localizable surrogate model of electrophysiological activity;
   training an adaptive classifier with said training field patterns;
   measuring a plurality of spatial field patterns outside of said subject, generated by electrophysiological activities in said subject, with a multi-channel measuring apparatus to obtain a plurality of respective measured field patterns;
   generating a plurality of feature vectors respectively representative of each measured field pattern;
   supplying said feature vectors to a plurality of inputs of said adaptive classifier;
   generating a probability value for each measured field pattern at an output of said classifier identifying a probability with which said that measured field pattern can be generated by a selected localizable surrogate model; and
   classifying said spatial field patterns dependent on said probability.

2. A method as claimed in claim 1 wherein the step of generating said feature vectors comprises generating said feature vectors in a pre-processing unit connected between said multi-channel measuring apparatus and said adaptive classifier.

3. A method as claimed in claim 2 comprising the additional step of conducting an amplitude normalization of measured values in each of said channels.

4. A method as claimed in claim 1 comprising the additional step of superimposing noise on the respective training field pattern from said at least one non-localizable surrogate model.

5. A method as claimed in claim 1 comprising the step of employing an at least two-layer neural network as said adaptive classifier, said neural network having a plurality of input neurons to which signals from said channels of said multi-channel measuring apparatus are supplied, and an output, forming said output of said adaptive classifier, at which said probability values for said field patterns are present.

6. A method as claimed in claim 5 wherein the step of employing an at least two-layer neural network as said adaptive classifier comprises employing a neural network having a plurality of input neurons equal to the number of channels of said multi-channel measuring apparatus.

7. A method as claimed in claim 5 wherein said multi-channel measuring apparatus has at least 30 channels, and wherein the step of employing said neural network comprises employing a neural network having a plurality of hidden neurons approximately equal to one and one-half the plurality of channels of said multi-channel measuring apparatus.

8. A method as claimed in claim 1 comprising the additional steps of:
connecting said multi-channel measuring apparatus and said output of said adaptive classifier to an image display unit; and
displaying a chronological curve of said field patterns together with a probability value for which the respective field patterns can be generated by said surrogate model on said image display unit.

9. A method as claimed in claim 1 comprising the additional steps of:
comparing said output of said adaptive classifier to a threshold;
forwarding said probability value from said output as a forwarded value if said probability value exceeds said threshold; and
forwarding a value of zero from said output as said forwarded value when said 10. A method as claimed in claim 9 comprising the additional step of:
setting said probability value to zero if said probability value fails to exceed said threshold for a minimum chronological duration.

11. A method as claimed in claim 9 further comprising the steps of:
weighting each signal in the respective channels of said multi-channel measuring apparatus with a weighting factor dependent on a plurality of positive field values and negative field values in a field pattern; and
multiplying said forwarded value from said output by said weighting factor to obtain a modified probability value.

12. A method as claimed in claim 1 wherein the step of measuring said electrophysiological activities comprises measuring biomagnetic field patterns.

13. A method as claimed in claim 1 comprising the additional step of:
defining said surrogate model as an electrical current dipole disposed in a space having a uniform electrical conductivity.

14. A method as claimed in claim 13 comprising the additional step of defining said space as a conductive sphere.

* * * * *